United States Patent
Butters (10) Patent No.: US 11,633,619 B2
(45) Date of Patent: Apr. 25, 2023

(54) SYSTEMS AND METHODS FOR MEASURING MAGNETIC FIELDS FROM SOLVATED TARGET MOLECULES USING A MAGNETORESISTIVE SENSOR

(71) Applicant: NearField Atomics Inc., Seattle, WA (US)

(72) Inventor: John T. Butters, Seattle, WA (US)

(73) Assignee: NEARFIELD ATOMICS INC., Seattle, WA (US)

( * ) Notice: Subject to any disclaimer, the term of this patent is extended or adjusted under 35 U.S.C. 154(b) by 0 days.

(21) Appl. No.: 17/695,482

(22) Filed: Mar. 15, 2022

(65) Prior Publication Data

US 2022/0296912 A1  Sep. 22, 2022

Related U.S. Application Data

(60) Provisional application No. 63/252,986, filed on Oct. 6, 2021, provisional application No. 63/164,022, filed on Mar. 22, 2021.

(51) Int. Cl.
  *G01N 27/74* (2006.01)
  *A61N 2/02* (2006.01)
  *A61K 41/00* (2020.01)

(52) U.S. Cl.
  CPC ............ *A61N 2/02* (2013.01); *A61K 41/0052* (2013.01); *G01N 27/74* (2013.01)

(58) Field of Classification Search
  None
  See application file for complete search history.

(56) References Cited

U.S. PATENT DOCUMENTS

| | | |
|---|---|---|
| 6,541,978 B1 | 4/2003 | Benveniste et al. |
| 6,724,188 B2 | 4/2004 | Butters et al. |
| 6,952,652 B2 | 10/2005 | Butters |
| 6,995,558 B2 | 2/2006 | Butters et al. |
| 7,048,890 B2 | 5/2006 | Coehoorn et al. |
| 7,081,747 B2 | 7/2006 | Butters et al. |

(Continued)

FOREIGN PATENT DOCUMENTS

| | | |
|---|---|---|
| DE | 102014218744 | 3/2016 |
| EP | 2109771 B1 | 6/2010 |

(Continued)

OTHER PUBLICATIONS

International Search Report and Written Opinion for PCT/US2022/017246 dated May 19, 2022.

(Continued)

*Primary Examiner* — Rebecca M Giere
(74) *Attorney, Agent, or Firm* — Branch Partners PLLC; Bruce E. Black (57) ABSTRACT

A measurement system includes a container configured to contain a solvated target molecule and at least one magnetoresistive (MR) sensor device including at least one MR sensor disposed near the container and configured to measure a magnetic field generated by the solvated target molecule, each of the at least one MR sensor including a pin layer having a pinned direction of magnetization, a free layer having a direction of magnetization that varies with an applied magnetic field, and a non-conductive layer separating the pin layer and the free layer.

20 Claims, 9 Drawing Sheets

(56) References Cited

U.S. PATENT DOCUMENTS

| | | |
|---|---|---|
| 7,412,340 B2 | 8/2008 | Butters |
| 8,456,157 B2 | 6/2013 | Litvinov et al. |
| 8,838,022 B2 | 9/2014 | Dobyns |
| 8,929,809 B2 | 1/2015 | Dobyns |
| 9,300,367 B2 | 3/2016 | Christensen et al. |
| 9,417,257 B2 | 8/2016 | Butters et al. |
| 9,455,771 B2 | 9/2016 | Dobyns |
| 9,742,471 B1 | 8/2017 | Thoen |
| 10,012,706 B2 | 7/2018 | Bates et al. |
| 10,015,623 B2 | 7/2018 | Thoen |
| 10,046,172 B2 | 8/2018 | Butters et al. |
| 10,210,409 B1 | 2/2019 | Migneco et al. |
| 11,103,721 B2 | 8/2021 | Butters et al. |
| 2004/0233060 A1 | 11/2004 | Mohri |
| 2005/0087000 A1* | 4/2005 | Coehoorn ............ B82Y 25/00 73/53.01 |
| 2010/0264917 A1 | 10/2010 | Budker et al. |
| 2010/0298624 A1 | 11/2010 | Becker |
| 2011/0244599 A1* | 10/2011 | Whig ................ G01R 33/098 257/E21.585 |
| 2012/0310550 A1 | 12/2012 | Bates et al. |
| 2014/0292318 A1 | 10/2014 | Wang et al. |
| 2016/0030761 A1* | 2/2016 | Butters ............... A61N 2/004 600/14 |
| 2017/0097337 A1 | 4/2017 | Schultz et al. |
| 2018/0237850 A1 | 8/2018 | Mandell et al. |
| 2019/0143135 A1 | 5/2019 | Butters |
| 2019/0184188 A1 | 6/2019 | Butters et al. |
| 2019/0317167 A1 | 10/2019 | Laborde et al. |
| 2020/0326309 A1 | 10/2020 | Braganca et al. |
| 2022/0226663 A1 | 7/2022 | Butters et al. |
| 2022/0257962 A1 | 8/2022 | Mogen et al. |

FOREIGN PATENT DOCUMENTS

| | | |
|---|---|---|
| EP | 2115468 B1 | 6/2010 |
| EP | 1566651 B1 | 6/2013 |
| EP | 2614770 | 7/2013 |
| EP | 2800970 B1 | 9/2016 |
| EP | 3695878 | 8/2020 |
| WO | 2019/070911 | 4/2019 |

OTHER PUBLICATIONS

Issadore D, Park YI, Shao H, Min C, Lee K, Liong M, Weissleder R, Lee H. Magnetic sensing technology for molecular analyses. Lab Chip. Jul. 21, 2014;14(14):2385-97. doi: 10.1039/c4lc00314d.

Oogane, M., Fujiwara, K., Kanno, A., Nakano, T., Wagatsuma, H., Arimoto, T., Mizukami, S., Kumagai, S., Matsuzaki, H., Nakasato, N., & Ando, Y. (2021). Sub-pT magnetic field detection by tunnel magneto-resistive sensors. Applied Physics Express, 14(12), [123002]. https://doi.org/10.35848/1882-0786/ac3809.

Richard S. Gaster; Giant Magnetoresistive Nanosensors for Ultrasensitive In Vitro Diagnostics and Biomolecular Kinetics. Dissertation submitted to Stanford University, Nov. 2011; 163 pages. Available on-line at https://purl.stanford.edu/jt093nq0893.

Adem S, Jain S, Sveiven M, Zhou X, O'Donoghue AJ, Hall DA. Giant magnetoresistive biosensors for real-time quantitative detection of protease activity. Sci Rep. May 14, 2020;10(1):7941. doi: 10.1038/s41598-020-62910-2. PMID: 32409675; PMCID: PMC7224196.

Wang, W., Wang, Y., Tu, L. et al. Magnetoresistive performance and comparison of supermagnetic nanoparticles on giant magnetoresistive sensor-based detection system. Sci Rep 4, 5716 (2014). https://doi.org/10.1038/srep05716.

Rizzi, G., Dufva, M. & Hansen, M. Magnetoresistive sensors for measurements of DNA hybridization kinetics—effect of TINA modifications. Sci Rep 7, 41940 (2017). https://doi.org/10.1038/srep41940.

Trisnanto, Suko & Kasajima, Tamon & Akushichi, Taiju & Takemura, Yasushi. (2021). Magnetic particle imaging using linear magnetization response-driven harmonic signal of magnetoresistive sensor. Applied Physics Express. 14. 10.35848/1882-0786/ac1d63.

Ioanna Giouroudi and Evangelos Hristoforou , "Perspective: Magnetoresistive sensors for biomedicine", Journal of Applied Physics 124, 030902 (2018) https://doi.org/10.1063/1.5027035.

Baselt DR, Lee GU, Natesan M, Metzger SW, Sheehan PE, Colton RJ. A biosensor based on magnetoresistance technology. Biosens Bioelectron. Oct. 1, 1998;13(7-8):731-9. doi: 10.1016/s0956-5663(98)00037-2. PMID: 9828367.

Yao, Li & Xu, Shoujun. (2014). Detection of magnetic nanomaterials in molecular imaging and diagnosis applications. Nanotechnology Reviews. 3. 247-268. 10.1515/ntrev-2013-0044.

Yin, T.-I & Paul, J. & Lehndorff, Ronald. (2016). 3.3.1—Magnetoresistive Sensors for the Application in Biotechnology. 190-194. 10.5162/sensoren2016/3.3.1.

Shirai Y, Hirao K, Shibuya T, Okawa S, Hasegawa Y, Adachi Y, Sekihara K, Kawabata S. Magnetocardiography Using a Magnetoresistive Sensor Array. Int Heart J. Jan. 25, 2019;60(1):50-54. doi: 10.1536/ihj.18-002. Epub Nov. 20, 2018. PMID: 30464123.

Smith, C.H., & Schneider, R.W. (2000). GMR and SDT Sensors and Arrays for LowField Magnetic Applications. Nonvolatile Electronics, Inc. 12 pages.

Bae, Seongtae. (2010). In-Vitro Magnetoresistive Biosensors for Single Molecular Based Disease Diagnostics: Optimization of Sensor Geometry and Structure. 10.5772/6870.

Henriksen, Anders & Ley, Mikkel & Flyvbjerg, Henrik & Hansen, Mikkel. (2015). Configurational Statistics of Magnetic Bead Detection with Magnetoresistive Sensors. PloS one. 10. e0141115. 10.1371/journal.pone.0141115.

Reiss, Guenter & Brückl, Hubert & Hutten, Andreas & Schotter, Joerg & Brzeska, Monika & Panhorst, Michael & Sudfeld, Daniela & Becker, Anke & Kamp, Paul-Bertram & Puehler, Alfred & Wojczykowski, Klaus & Jutzi, Peter. (2004). Magnetoresistive Sensors and Magnetic Nanoparticles for Biotechnology. Journal of Materials Research. 20. 3294-3302. 10.1557/PROC-853-I9.1.

Su D, Wu K, Saha R, Peng C, Wang JP. Advances in Magnetoresistive Biosensors. Micromachines (Basel). Dec. 26, 2019;11(1):34. doi: 10.3390/mi11010034. PMID: 31888076; PMCID: PMC7019276.

Ulasov IV, Foster H, Butters M, Yoon JG, Ozawa T, Nicolaides T, Figueroa X, Hothi P, Prados M, Butters J, Cobbs C. Precision knockdown of EGFR gene expression using radio frequency electromagnetic energy. J Neurooncol. Jun. 2017;133(2):257-264. doi: 10.1007/s11060-017-2440-x. Epub Apr. 22, 2017. PMID: 28434113.

Butters, John & Figueroa, Xavier & Butters, Bennett. (2014). Non-Thermal Radio Frequency Stimulation of Tubulin Polymerization in Vitro: A Potential Therapy for Cancer Treatment. Open Journal of Biophysics. 04. 147. 10.4236/ojbiphy.2014.44015.

Mukthavaram R, Jiang P, Nomura N, et al. ATPS-64: Preclinical Studies Using Nativis Voyager RFE System, a Novel Non-Invasive, Low Energy, Non-Thermal, Non-Ionizing Radiofrequency Energy (RFE) Device in Glioblastoma Mouse Models. Neuro Oncol. 2015;17(Suppl 5):v32. doi:10.1093/neuonc/nov204.64.

Cobbs C, McClay E, Duic JP, Nabors LB, Morgan Murray D, Kesari S. An early feasibility study of the Nativis Voyager® device in patients with recurrent glioblastoma: first cohort in US. CNS Oncol. Mar. 2019;8(1):CNS30. doi: 10.2217/cns-2018-0013. Epub Dec. 14, 2018. PMID: 30547676; PMCID: PMC6499016.

Murphy M, Dowling A, Thien C, Priest E, Morgan Murray D, Kesari S. A feasibility study of the Nativis Voyager® device in patients with recurrent glioblastoma in Australia. CNS Oncol. Mar. 2019;8(1):CNS31. doi: 10.2217/cns-2018-0017. Epub Feb. 7, 2019. PMID: 30727742; PMCID: PMC6499017.

Ulasov, Ilya & Ghosh, Dhimankrishna & Butters, Mike & Butters, John & Cobbs, Charles. (2016). EXTH-50. Specific Knockdown of EGFR and PLK1 Gene Expression in U87 GBM Cells With Radiofrequency Energy (RFE) Device. Japan Society for Neuro-Oncology. 18. vi70-vi70. 10.1093/neuonc/now212.292.

Butters, Bennett & Vogeli, Gabriel & Figueroa, Xavier. (2017). Non-Thermal Radio Frequency Stimulation Inhibits the Tryptophan Synthase Beta Subunit in the Algae Chlamydomonas reinhardtii. Open Journal of Biophysics. 07. 82-93. 10.4236/ojbiphy.2017.73007.

(56) References Cited

OTHER PUBLICATIONS

Figueroa, Xavier; Green, Yesenia; Murray, Donna Morgan; and Butters, Mike. Effects of Magnetic Fields on Biological Systems, An Overview. EMulate Therapeutics, Mar. 6, 2020. 8 pages.
Figueroa, Xavier & Butters, Mike & Donnell, Scott. (2019). SCIDOT-47. Effect of uIRFE Cognates Emulating Bioactive Substances on Animal Behavior. Neuro-Oncology. 21. vi281-vi282. 10.1093/neuonc/noz175.1183.
Specification of U.S. Appl. No. 17/677,269, filed Feb. 22, 2022.
Press Release for "Hapbee Announces Filing of Provisional Patent Application for Bed-Related Form Factor," Feb. 19, 2021, found at https://hapbee.com/blogs/hapbee/hapbee-announces-filing-of-provisional-patent-application-for-bed-related-form-factor.
International Search Report and Written Opinion for PCT Application No. PCT/US2022/020384 dated Jun. 29, 2022.

\* cited by examiner

Fig. 11

SYSTEMS AND METHODS FOR MEASURING MAGNETIC FIELDS FROM SOLVATED TARGET MOLECULES USING A MAGNETORESISTIVE SENSOR

CROSS-REFERENCE TO RELATED APPLICATIONS

This patent application claims priority to U.S. Provisional Application Ser. No. 63/164,022, filed Mar. 22, 2021, and U.S. Provisional Application Ser. No. 63/252,986, filed Oct. 6, 2021, both of which are incorporated herein by reference.

FIELD

The present invention is directed to the area of systems and methods for measuring magnetic fields. The present invention is also directed to systems and methods for measuring magnetic fields from solvated target molecules using a magnetoresistive sensor, as well as systems and methods for delivery of therapy using the measured magnetic fields.

BACKGROUND

Ultra-low radio frequency energy therapy is based on measurement of the unique electrostatic potential of a target molecule. The unique and specific ultra-low radio frequency energy is used to induce electron and charge transfer in a defined bioactive target, altering cell dynamics to produce a therapeutic response. In at least some embodiments, to provide therapy, an ultra-low radio frequency energy cognate of a target molecule is delivered locally and non-systemically via a medical device. To provide the therapy, the ultra-low radio frequency energy cognate must be obtained.

BRIEF SUMMARY

One embodiment is a measurement system that includes a container configured to contain a solvated target molecule and at least one magnetoresistive (MR) sensor device including at least one MR sensor disposed near the container and configured to measure a magnetic field generated by the solvated target molecule, each of the at least one MR sensor including a pin layer having a pinned direction of magnetization, a free layer having a direction of magnetization that varies with an applied magnetic field, and a non-conductive layer separating the pin layer and the free layer.

In at least some embodiments, the at least one MR sensor device is a single MR sensor device. In at least some embodiments, the at least one MR sensor device is a plurality of MR sensor devices. In at least some embodiments, the plurality of MR sensor devices are arranged in a plane around the container. In at least some embodiments, the MR sensor devices are arranged along at least three orthogonal directions with respect to the container.

In at least some embodiments, each of the at least one sensor device includes a plurality of the MR sensors. In at least some embodiments, the plurality of MR sensors are arranged in a Wheatstone bridge.

Another embodiment is a method that includes solvating a target molecule and placing the solvated target molecule in a container; providing the container with the solvated target molecule in a measurement system including at least one magnetoresistive (MR) sensor device including at least one MR sensor disposed near the container and configured to measure a magnetic field generated by the solvated target molecule, each of the at least one MR sensor including a pin layer having a pinned direction of magnetization, a free layer having a direction of magnetization that varies with an applied magnetic field, and a non-conductive layer separating the pin layer and the free layer; applying a stimulus to the solvated target molecule; using the at least one MR sensor of the at least one MR sensor device to acquire a magnetic field generated by the solvated target molecule in response to the stimulus; and producing signals by the at least one MR sensor of the at least one MR sensor device in response to the acquired magnetic field.

In at least some embodiments, the method further includes amplifying the signals from the at least one MR sensor of the at least one MR sensor device and converting the amplified signals into digital signals. In at least some embodiments, the method further includes delivering the digital signals to a delivery device to simulate the presence of the solvated target molecule. In at least some embodiments, the method further includes storing the digital signals as a data file in an audio file format.

In at least some embodiments, the at least one MR sensor device is a single MR sensor device. In at least some embodiments, the at least one MR sensor device is a plurality of MR sensor devices. In at least some embodiments, the plurality of MR sensor devices are arranged in a plane around the container. In at least some embodiments, the MR sensor devices are arranged along at least three orthogonal directions with respect to the container.

In at least some embodiments, each of the at least one sensor device includes a plurality of the MR sensors. In at least some embodiments, the plurality of MR sensors are arranged in a Wheatstone bridge.

A further embodiment is a therapy delivery system that includes any of the measurement systems described above; a near field magnetic induction (NFMI) transceiver device configured to be worn or otherwise disposed on a patient and configured to utilize the measured magnetic field of the measurement system to produce signals for delivery of therapy, the NFMI transceiver device comprising a NFMI transceiver; and a therapy delivery device including a NFMI receiver configured to receive the signals from the NFMI transceiver device, and a therapy delivery circuit configured to deliver a therapeutic magnetic signal, based, at least in part, on the received signals from the NFMI transceiver device, to the patient when the patient wears the therapy delivery device or has the therapy delivery device disposed on skin of the patient or has the therapy delivery device implanted.

In at least some embodiments, the NFMI transceiver device further includes a communications circuit for communication, other than NFMI, to a user device. In at least some embodiments, the therapy delivery system further comprises the user device configured to communicate with the NFMI transceiver device through the communications circuit of the NFMI transceiver device.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of systems and methods for measuring magnetic fields. The present invention is also directed to systems and methods for measuring magnetic fields from solvated target molecules using a magnetoresistive sensor, as well as systems and methods for delivery of therapy using the measured magnetic fields.

The signals for delivery of ultra-low radio frequency energy can be generated from measurements of electromagnetic characteristics of one or more target molecules, such as the unique electrostatic potential of a target molecule. Every molecule has a unique electrostatic surface potential. This potential influences how a molecule interacts with proteins and other biological agents. Electron and charge transfer are central to many biological processes and are a direct result of interacting surface potentials. Artificial electromagnetic fields (e.g., the ultra-low radio frequency energy) are capable of triggering a similar receptor response and conformational change in the absence of a physical drug or molecular agonist.

In at least some embodiments, the unique and specific ultra-low radio frequency energy is used to induce electron and charge transfer in a defined bioactive target, altering cell dynamics to produce a therapeutic response. In at least some embodiments, to provide therapy, an ultra-low radio frequency energy cognate of a target molecule is delivered locally and non-systemically via a delivery device. Preclinical and clinical studies suggest that ultra-low radio frequency energy therapy provides the ability to specifically regulate metabolic pathways and replicate known mechanisms of action for proven commercial drugs or other molecules.

Examples of devices and systems for measuring or using ultra-low radio frequency energy can be found in U.S. Pat. Nos. 6,541,978; 6,724,188; 6,952,652; 6,995,558; 7,081,747; 7,412,340; 8,838,022; 8,929,809; 9,300,367; 9,417,257; 9,455,771; 9,742,471; 10,015,623; 10,046,172; and 11,103,721; U.S. patent application Ser. Nos. 17/320,144 and 17/677,269; U.S. Provisional Patent Application Ser. Nos. 63/154,532; 63/164,022; and 63/252,986; U.S. Patent Application Publications Nos. 2019/0143135 and 2019/0184188; and PCT Patent Application Publication WO 2019/070911, all of which are incorporated herein by reference in their entireties.

In at least some embodiments, the delivery of ultra-low radio frequency energy includes the generation of a magnetic field having a field strength of up to 1 Gauss, for example, in the range of 20 to 40 mG. In at least some embodiments, the delivery of ultra-low radio frequency energy includes the generation of a magnetic field having a field strength of up to 8 Gauss. In at least some embodiments, the delivery of ultra-low radio frequency energy includes the generation of a therapeutic magnetic signal having a frequency in the range of 0.1 Hz to 22 kHz, in the range of 0.1 to 10 kHz, or in the range of 8 Hz to 22 kHz.

An example of affecting biologic activity with ultra-low radio frequency energy fields includes experiments conducted to demonstrate the specificity and cellular effects of a specific ultra-low radio frequency energy targeting epidermal growth factor receptor, EGFR, on glioblastoma cell line U-87 MG. At 118 and 72 hours, EGFR inhibition by the ultra-low radio frequency energy reduced the level of EGFR protein by 27% and 73%, respectively. These data indicate that ultra-low radio frequency energy can inhibit gene expression at the transcriptional and protein levels, similar to what is observed with physical small interfering RNA (siRNA) inhibition. Specific EGFR knockdown effect was detected in U-87 MG cells treated with ultra-low radio frequency energy using an 80 gene PCR-based array. See, "Effects of Magnetic Fields on Biological Systems An Overview"; X. Figueroa, Y. Green, D. M. Murray, and M. Butters; EMulate Therapeutics; Mar. 13, 2020.

In another example, ultra-low radio frequency energy therapy was provided as a cancer treatment for over 400 dogs (pets) with naturally occurring malignancies. Interim review of the first 200 pets observed partial responses and complete responses in over 20 different tumor types. No clinically important or significant toxicities (Grade 3 or 4) were observed.

Conventionally, superconducting quantum interference devices (SQUID) have been used to measure electromagnetic characteristics of molecules, such as the unique electrostatic potential of the molecules. SQUIDs, however, can be bulky, expensive, and require cryogenic fluids for operation.

As described herein, a magnetoresistive (MR) sensor can be used in a single or multi-channel configuration to measure the electromagnetic characteristics of a molecule, such as, for example, the magnetic field of a solvated target molecule, and produce measurement signals. The measurement signals are processed and stored (for example, as a 24-bit WAV file) for uses such as, for example, therapy or drug discovery. In at least some embodiments, the bandwidth of the stored measurement signals is in a range from DC to 22 kHz or more. In at least some embodiments, the delivery of ultra-low radio frequency energy includes the generation of a therapeutic magnetic signal having one or more frequencies (or ranges/bands of frequencies) in the range of 0.1 Hz to 22 kHz, in the range of 1 Hz to 22 kHz, or in the range of 0.1 to 10 kHz.

In at least some embodiments, the measurement signals can be processed and stored as a data file in audio file format (for example, a WAV, PCM, AIFF, MP3, AAC, WMA, FLAC, ALAC, MIDI, APE, MP2, M4A, AAC, VQF, AMR, AC3, RA, 3GA, OGG, ASF, DSD, or MQA file format, or any other suitable format). Audio file formats may be particularly useful as these formats are used to store multi-frequency information for generating electromagnetic signals. A WAV file is used herein as an example of the data file for storage and delivery of the signals to produce ultra-low radio frequency energy. A suitable resolution can be used including, but not limited to, 16, 24, or 32 bit resolution.

In at least some embodiments, the signals for delivery of ultra-low radio frequency energy can be generated from measurements made using one or more particular target molecules. These measurements can be, for example, processed, converted from analog to digital signals, and stored for delivery using any suitable delivery device. The molecule(s) used to obtain the signals can be any suitable drug molecule(s), therapeutic molecule(s), other molecule(s) that produce(s) a physiological or biological response, or the like.

In at least some embodiments, a delivery device for the ultra-low radio frequency energy can use any suitable method of delivery of the signals from the data file including, but not limited to, analog or digital modulation for signal transmission. Any suitable modulation technique can be used including, but not limited to, any type of amplitude, frequency, phase, or other modulation.

Figure 1:
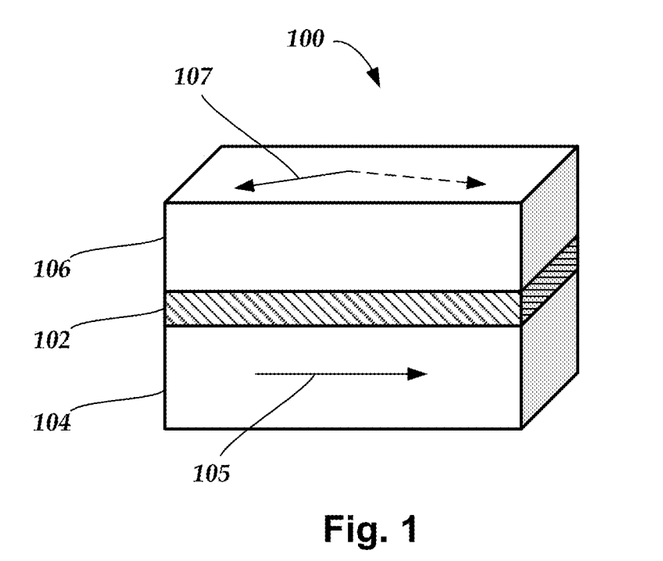
FIG. 1 is a diagram of one embodiment of a magnetoresistive (MR) sensor.

FIG. 1 illustrates one embodiment of a magnetoresistive (MR) sensor 100 (which is also known as a tunnel magnetoresistive (TMR) sensor or magnetic tunnel junction (MTJ) sensor) that includes a thin film 102 of non-magnetic material between two ferromagnetic films that form a pin layer 104 and a free layer 106, respectively. The pin layer 104 has a direction of magnetization 105 that is pinned. Pinning can be accomplished by a variety of methods including, but not limited to, forming the pin layer 104 of a material in a defined crystal structure. The direction of magnetization 107 of the free layer 106 follows the direction of an external magnetic field. For example, the free layer 106 can be formed of a material in an amorphous (e.g., non-crystalline) structure. Examples of MR devices are found in, for example, European Patent Application No. EP 2614770, incorporated herein by reference in its entirety.

The electrical resistance of the magnetoresistive sensor 100 varies (in at least some embodiments, proportionally) with the relative angle between the directions of magnetization in the pin layer 104 and the free layer 106. Thus, by observing the resistance of the magnetoresistive sensor 100, the direction of the external magnetic field, which affects the direction of magnetization 107 of the free layer 106, can be determined.

Figure 2:
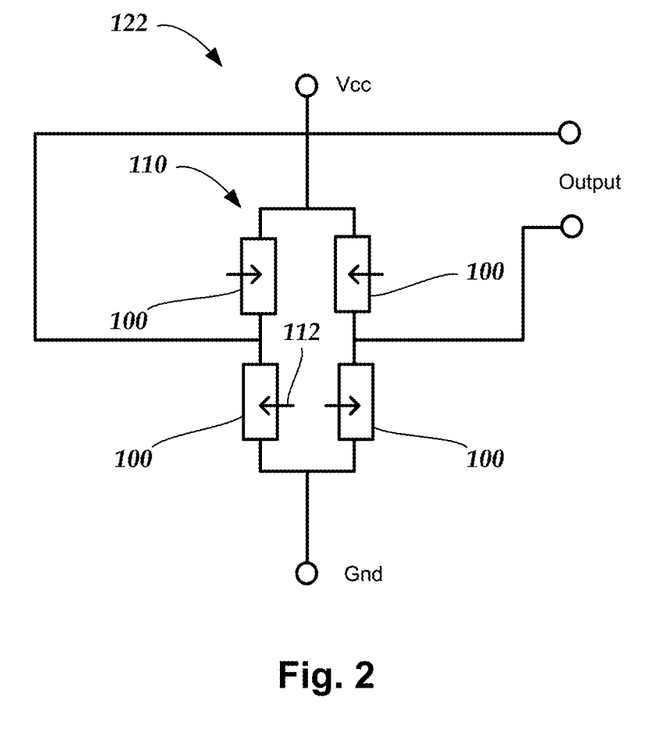
FIG. 2 illustrates one embodiment of an arrangement of MR sensors in a Wheatstone bridge for temperature compensation.

One or more MR sensors 100 can be used to measure the magnetic field by coupling to a DC power source. In FIG. 2, a MR sensor device 122 includes a Wheatstone bridge arrangement 110 of four MR sensors 100 (where the arrows 112 indicate the direction of magnetization of the pin layer 106) can be used for differential temperature compensation. One example of a MR sensor device that utilizes the MR sensors 100 is the TDK Nivio xMR Sensor (TDK Corporation, Tokyo, Japan).

Figure 3:
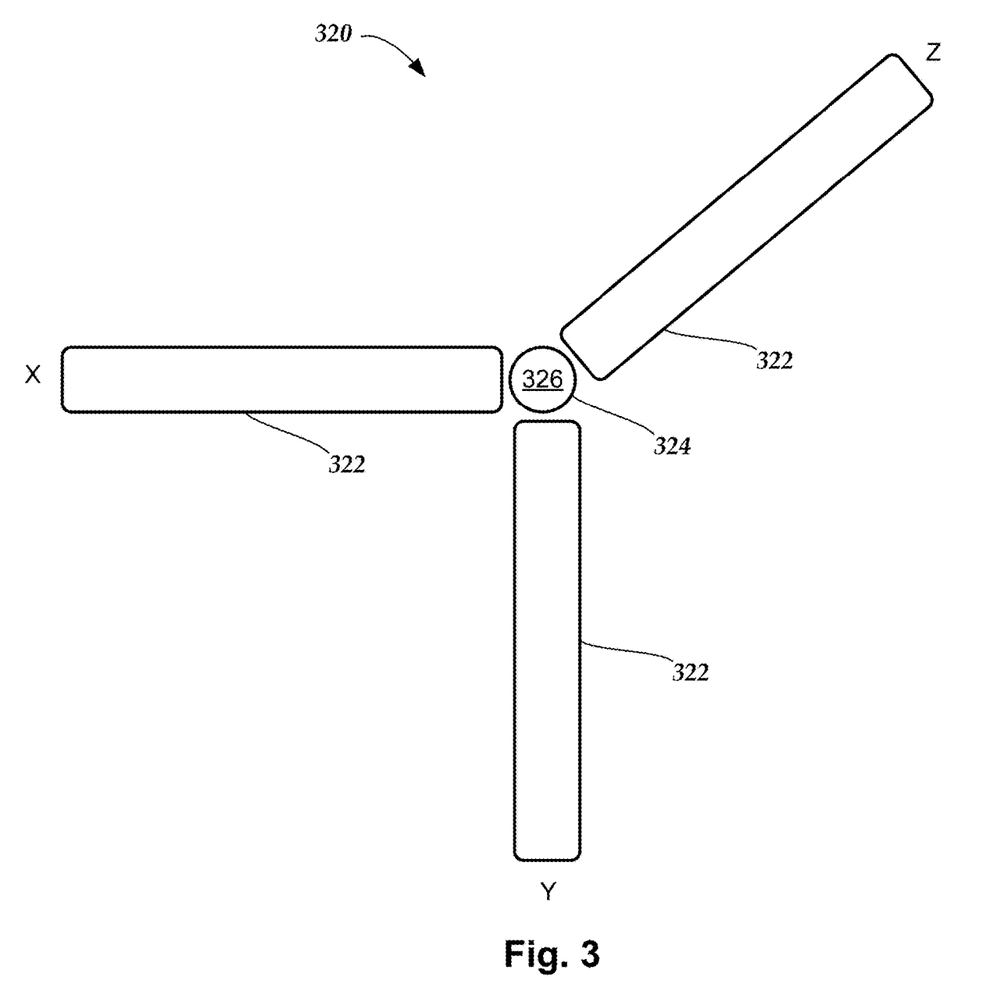
FIG. 3 is a schematic diagram of one embodiment of an arrangement of MR sensor devices around a container of solvated target molecule, according to the invention.

FIG. 3 illustrates one embodiment of a sensor arrangement 320 with multiple MR sensor devices 322 disposed around a container 324 with the target molecule 326 solvated in a solvent (for example, water, saline, plasma, or blood). The target molecule 326 can be any suitable target including, but not limited to, drug molecules (e.g., Taxol), oligonucleotides (e.g., RNA, mRNA, or the like), or any combination thereof.

In the illustrated embodiment of FIG. 3, a different MR sensor device 322 is positioned at each of the x, y, and z axes to measure the magnetic field arising from the electrostatic potential of the target molecule. Such measurement may include, for example, injecting noise into the sample in the container and recording the resulting magnetic field, as described in the references cited above. In at least some embodiments, the MR sensor device 322 can be a single MR sensor 100 or can be multiple MR sensors 100 arranged in the bridge illustrated in FIG. 2 or any other suitable arrangement.

Figure 4:
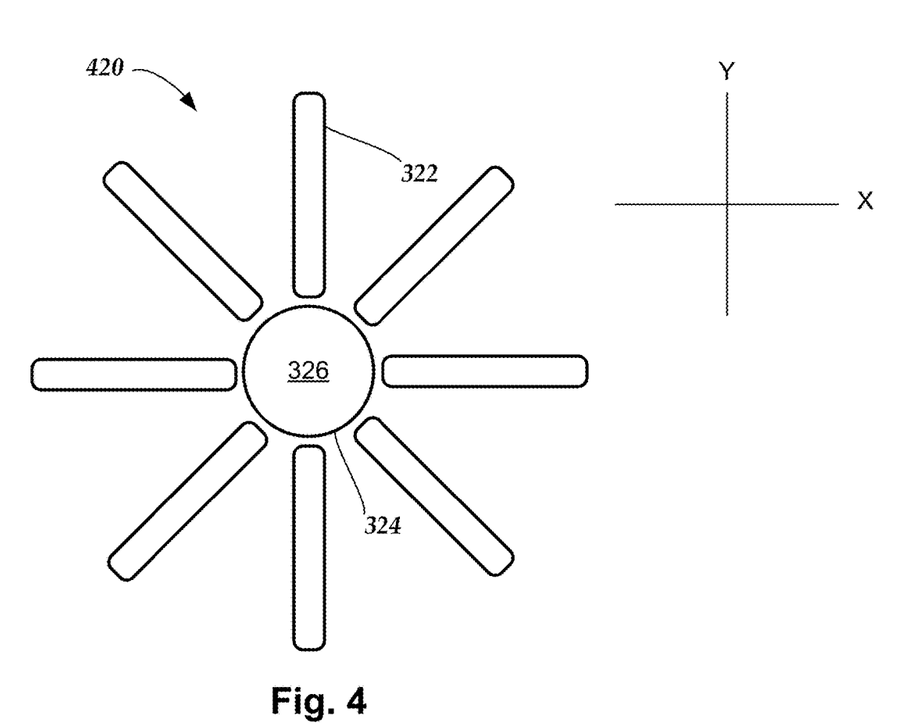
FIG. 4 is a schematic diagram of another embodiment of an arrangement of MR sensor devices around a container of solvated target molecule, according to the invention.

FIG. 4 illustrates another embodiment of a sensor arrangement 420 with multiple MR sensor devices 322 disposed around the container 324 holding the solvated target molecule. In this particular arrangement, eight MR sensor devices 322 are arranged around in the container in the x-y plane. Any other suitable two-dimensional arrangement of multiple (e.g., three, four, six, eight, ten, twelve, or more or any other suitable number) MR sensor devices 322 can be used.

Figure 5:
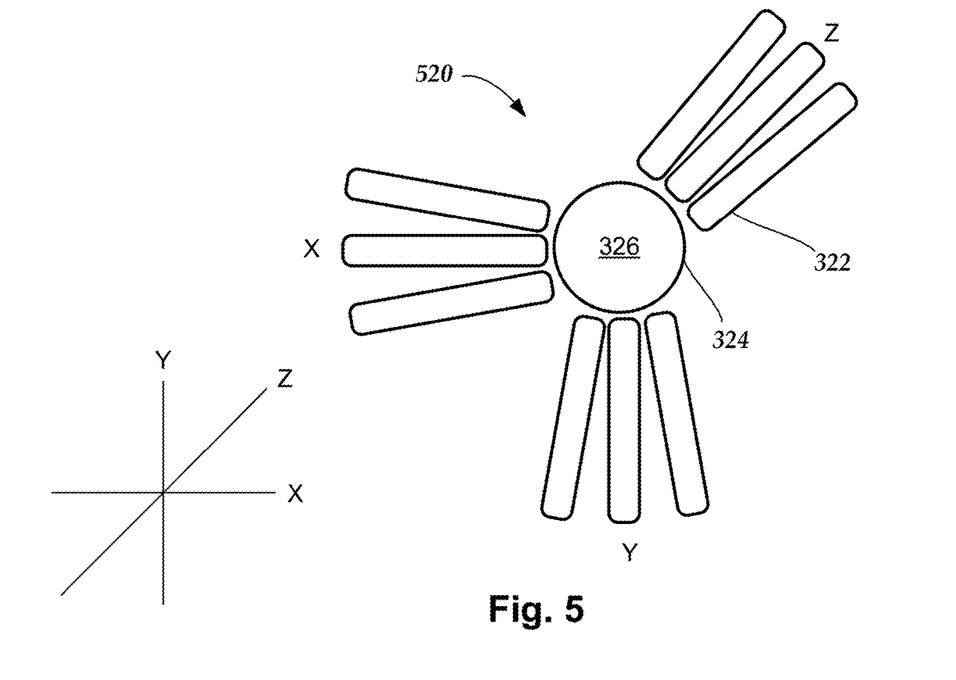
FIG. 5 is a schematic diagram of a third embodiment of an arrangement of MR sensor devices around a container of solvated target molecule, according to the invention.

FIG. 5 illustrates a further embodiment of a sensor arrangement 520 with multiple (e.g., three, four, six, eight, ten, twelve, or more or any other suitable number) MR sensor devices 322 disposed around the container 324 with the solvated target molecule. In this particular arrangement, three MR sensor devices 322 are arranged around each of the x, y, and z axes. It will be recognized that other three-dimensional arrangements of MR sensor devices (or any other magnetic field sensor devices) can be used including, for example, providing the arrangement illustrated in FIG. 4 along multiple planes (for example, the x-y plane and the y-z plane).

The arrangements of MR sensor devices 322 illustrated in FIGS. 3, 4, and 5 are examples of multi-channel configurations for recording electromagnetic characteristics (for example, the electrostatic potential) of a target molecule. It will be understood that single channel configurations with a single MR sensor device (or multiple MR sensor devices positioned together) can also be used.

It will also be understood that other magnetic field sensor devices can be used in a two-dimensional or three-dimensional arrangement (such as, but not limited to, those illustrated in FIGS. 3, 4, and 5) for recording the electromagnetic characteristics (for example, the electrostatic potential) of a target molecule. These arrangements can include one or more MR sensor devices 322, SQUIDs, optically pumped magnetometers (OPMs), other magnetometer sensors (for example, nitrogen vacancy magnetometers), any other suitable magnetic field sensor, or the like or any combination thereof.

Figure 6:
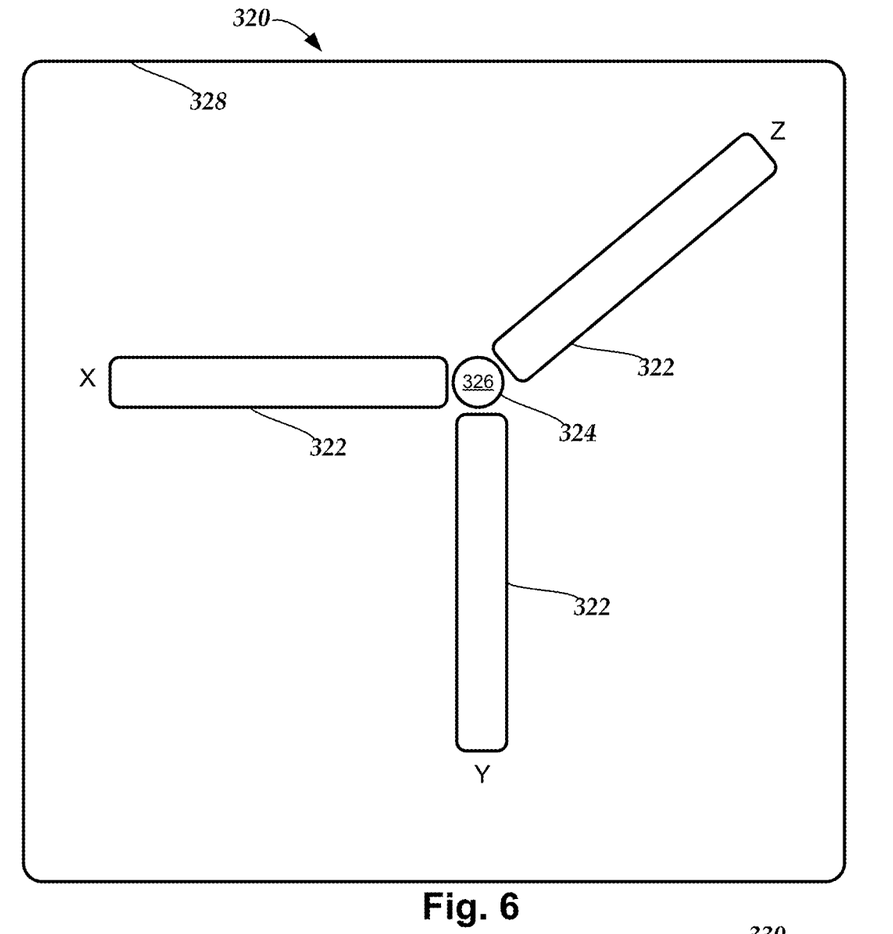
FIG. 6 is a schematic diagram of the arrangement of MR sensor devices around a container of solvated target molecule of FIG. 3 inside a shield, according to the invention.

FIG. 6 illustrates the sensor arrangement 320 disposed within a shield 328 to reduce or remove the ambient magnetic field (such as the Earth's magnetic field) within the shield. The shield can be a passive shield (for example, made of mu-metal or other shielding material or a Faraday cage or the like) or an active shield (for example, one or more magnetic field generators to counter the ambient magnetic field) or any combination thereof.

Figure 7A:
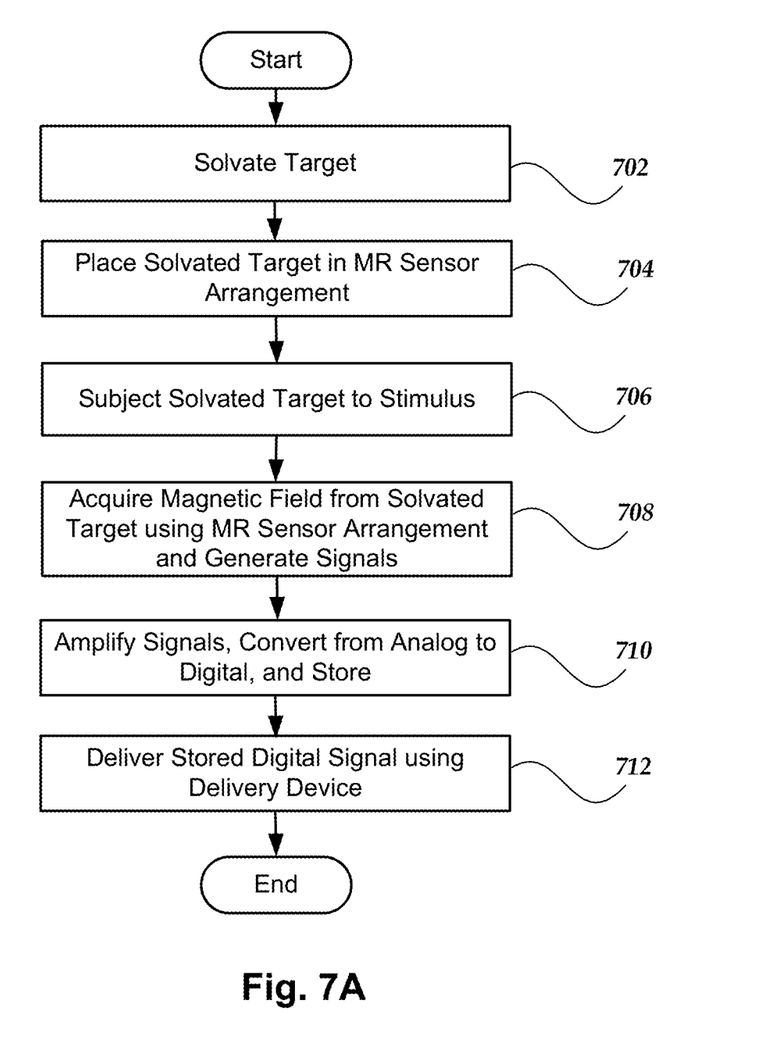
FIG. 7A is a flowchart of one embodiment of a workflow for generating and employing ultra-low radio frequency energy using MR sensor devices, according to the invention.

FIG. 7A is a flowchart of one embodiment of a workflow for generating and employing ultra-low radio frequency energy using the MR sensor devices described herein (or any other suitable magnetic field sensors.) In step 702, the target molecule is solvated in a solvent, such as, for example, water, saline, plasma, or blood. In step 704, the solvated target is placed in a MR sensor arrangement, such as one of the arrangements illustrated in FIG. 3, 4, or 5, or any other multi-channel or single channel configuration or arrangement. Optionally, a DC offset field (e.g., a voltage difference) can be applied to the solvated target to align the molecules along a particular direction defined by the DC offset field.

In step 706, in at least some embodiments, the solvated target is subjected to a stimulus (for example, noise or other suitable signal) to elicit a response. Optionally, white noise can be injected to enhance the response.

In step 708, the MR sensor devices of the MR sensor arrangement acquires the magnetic field generated by the solvated target. The MR sensor devices generate signals based on the acquired magnetic field.

In step 710, the signals from the MR sensor devices are amplified or otherwise processed, converted from analog to digital signals, and stored. In at least some embodiments, the signals can be processed using auto- or cross-correlations. Any other suitable signal processing techniques can be used.

In step 712, the stored digital signals are then provided to a delivery device, such as a therapy delivery device, to deliver the signals to a target and elicit the desired response based on the initial target molecule. In at least some embodiments, the delivery of ultra-low radio frequency energy includes the generation of a magnetic field having a field strength of up to 1 Gauss.

Figure 7B:
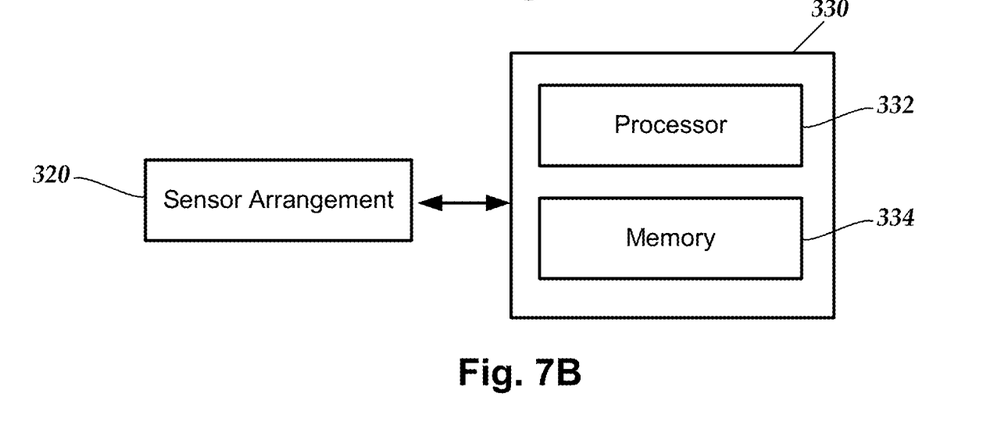
FIG. 7B is a block diagram of one embodiment of a system for measurement and signal processing system, according to the invention.

FIG. 7B illustrates one embodiment of a measurement and signal processing system. The system includes any suitable sensor arrangement 320 (with, or capable of receiving, the solvated target molecule 326 in a container 324, as illustrated in FIGS. 3 to 6) and a computing arrangement 330 for directing and receiving the measurements of the sensor arrangement. The computing arrangement 330 includes at least one processor 332 for directing the measuring, obtaining signals from the sensor arrangement, and processing the signals and at least one memory 334 for storing instructions for the processor and for storing the signals or the processed signals (for example, as a data file that is optionally in an audio file format.) Any suitable processor 332 can be used including, but not limited to, microprocessors, application specific integrated circuits (ASICs), other integrated circuits, or the like or any combination thereof. Any suitable memory 334 can be used including, but not limited to, RAM, ROM, EEPROM, flash memory, or the like or any combination thereof. The processor 332 or the memory 334 (or both) can be local or non-local to the sensor arrangement or can be distributed.

A variety of therapy delivery devices and therapy delivery systems can be used to deliver ultra-low radio frequency energy that based on the measurements or signals obtained using the MR sensor devices (or any other suitable magnetic field sensors), as described above. In at least some embodiments, a therapy delivery system can utilize NFMI to communicate with, and optionally control, one or more therapy delivery devices or sensors or any combination thereof. Near Field Magnetic Induction (NFMI) is a short-range wireless communication technology that utilizes magnetic fields for inductive transmission between coils or transducers in individual devices, in contrast to many conventional communications techniques that utilize electrical transmission through antennas. In at least some embodiments, NFMI can be superior to electrical/antenna transmission technologies for body-area networks, such as WBAN, because NFMI is attenuated less by the body than many electrical/antenna transmission technologies. Also, NFMI signals are attenuated more strongly over distance (in at least some cases, approximately by a factor of $1/r^6$ where r is distance) than a number of other conventional transmission technologies and, therefore, NFMI may provide a more private network that is substantially limited to the body of the patient. This can reduce interference or privacy breaches. In at least some embodiments, NFMI is more power efficient than other wireless technologies such as Bluetooth™, near field communication (NFC), or the like and may have lower power consumption than these technologies for transmitting the same data or signals. In addition to communication using NFMI, in at least some embodiments, the same coils can be used for wireless charging of device batteries or other power sources using magnetic induction.

Figure 8:
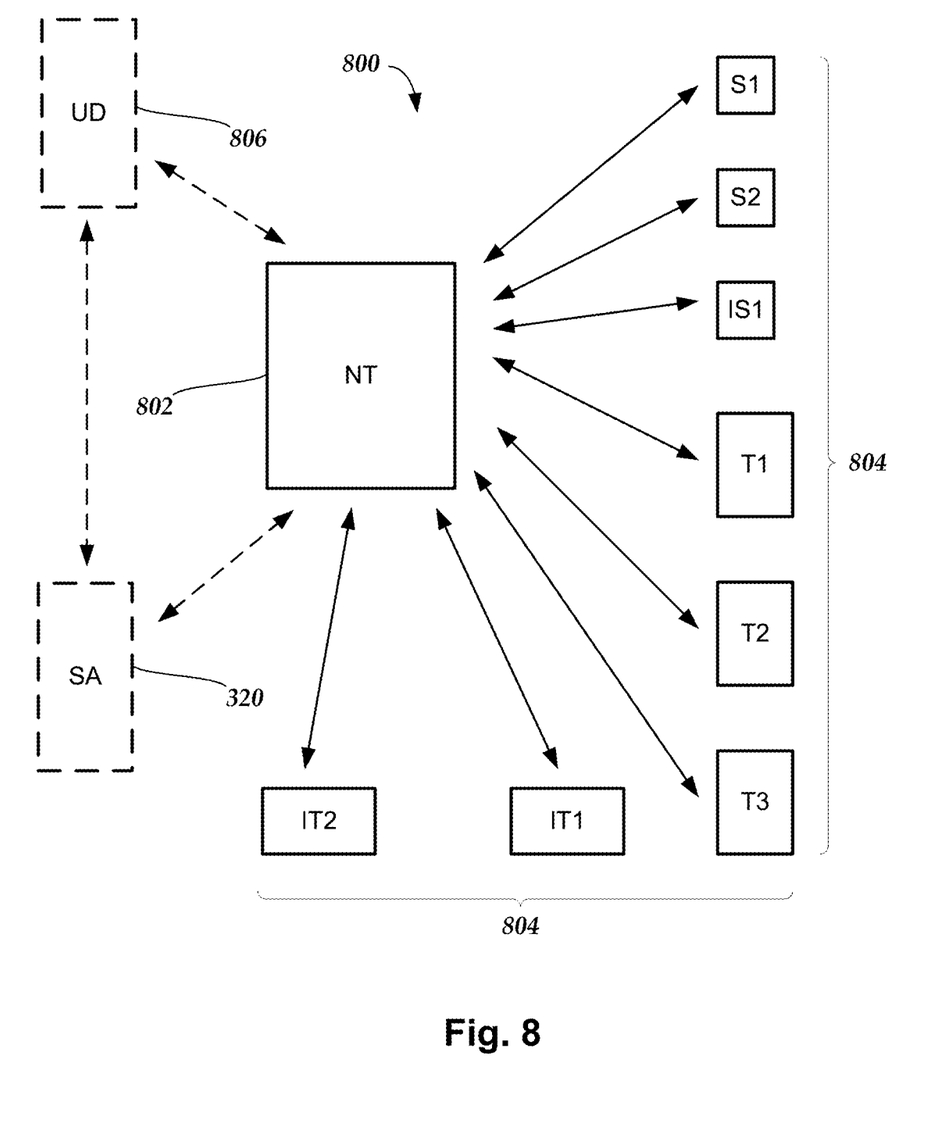
FIG. 8 is a block diagram of one embodiment of a system for delivering therapy using devices that communicate through near field magnetic induction (NFMI), according to the invention.

FIG. 8 illustrates one embodiment of a therapy delivery system 800 that includes a NFMI transceiver device 802 (NT) and one or more system devices 804 that can be therapy delivery devices (for example, devices T1, T2, T3, IT1, and IT2), sensors (for example, sensors S1, S2, and IS1), or the like or any combination thereof. Examples of sensors include, but are not limited to, the magnetoresistive sensor 100 (FIG. 1) or MR sensor devices 322 (FIGS. 3 to 5); temperature sensors such as thermistors or infrared sensors; piezoelectric or other pressure sensors (to measure, for example, blood pressure, pulse rate, inhalation/expiration, or other physical parameters); fluid sensors such as sweat sensors or blood sensors (for example, glucose sensors); pH sensors; cameras; microphones; healing detection sensors; or the like or any combination thereof.

The therapy delivery system 800 can optionally include one or more user devices 806 (UD) which may be, for example, a mobile device (such as a mobile phone, tablet, laptop, personal data assistant, or the like), a computer (for example, a laptop, a desktop computer, a server, or the like), a dedicated programming or monitoring device, or the like or any combination thereof. A user device 806 can, for example, direct operation of, or control, the NFMI transceiver device 802 or one or more of the system device 804 or any combination thereof; program the NFMI transceiver device 802 or one or more of the system device 804 or any combination thereof process or analyze data from any of the system devices 804; transmit data or other information to other devices, such as a computer or server at a healthcare facility; provide information to a user or patient on a screen of the user device 806; or the like or any combination thereof. In at least some embodiments, the delivery of therapy or the programming or alteration of therapy parameters may be restricted to a user with credentials, such as a password or other identification. The user device 806 may include one or more programs, applications, or features that provide these functions. In at least some embodiments, the NFMI transceiver device 802 can also perform one or more of these functions of a user device 806.

As also illustrated in FIG. 8, the therapy delivery system 800 can optionally include a sensor arrangement (SA) 320 (or one or more MR sensor devices 122, 322) to acquire or measure the magnetic field to produce signals that will be processed or otherwise used for the therapy as described above. In at least some embodiments, the sensor arrangement 320 is coupled directly to the NFMI transceiver device 802 or the user device 806 or both. It will be understood that the sensor arrangement 320 may also not be part of the therapy delivery system 800, but may be an independent system for measuring a magnetic field, as described above, and signals arising from the measurement of the magnetic field can then be processed, stored, distributed, or otherwise provided to the therapy delivery system 800 (e.g., to the NFMI transceiver device 802, the user device 806, the therapy deliver devices (for example, devices T1, T2, T3, IT1, and IT2), or any combination thereof.)

The NFMI transceiver device 802 communicates with the one or more system devices 804 by NFMI. In at least some embodiments, the NFMI transceiver device 802 and one or more system devices 804 create a Wireless Body Area Network (WBAN) with NFMI transmission. The development of new sensors and therapy delivery devices, as well as miniaturization of previously developed sensors and therapy delivery devices, provides an opportunity for monitoring of health conditions of patients. Such monitoring may be continuous or periodic and may be available at home or elsewhere, instead of being relegated to a healthcare facility. The use of wireless connectivity technologies can facilitate operation of, and data collection from, sensors and therapy delivery devices. The creation of a single body central gateway, such as a Wireless Body Area Network (WBAN), to transmit or receive from one or more therapy delivery devices or sensors can enhance this operation and data collection. The use of a WBAN can facilitate the collection of data for patient treatment of diseases or disorders, such as, for example, chronic diseases, like diabetes mellitus, cardiovascular diseases, respiratory diseases, cancer, other serious diseases, or the like. In at least some embodiments, data can be further exchanged between the patient and a healthcare provider (for example, a doctor, surgeon, clinic, hospital, or the like or any combination thereof). Such exchanges may facilitate mobile health (mHealth) or Telehealth services and applications.

Figure 9:
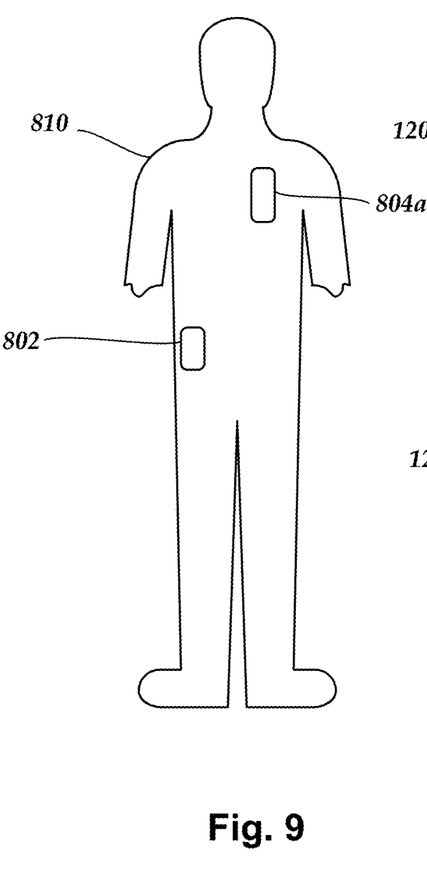
FIG. 9 illustrates one embodiment of a positioning of a NFMI transceiver device and a therapy delivery device on the body of a patient, according to the invention.

In at least some embodiments, the NFMI transceiver device 802 can be worn or carried by the patient. Each of the system devices 804 can be independently disposed on the patient, worn by the patient, or implanted in the patient. Devices 804 labeled IS1 and IT1/IT2 are an implanted sensor and implanted therapy devices, respectively. FIG. 9 illustrates one example of a NFMI transceiver device 802 worn by the patient 810 and a therapy delivery device 804a positioned on the patient.

Figure 10:
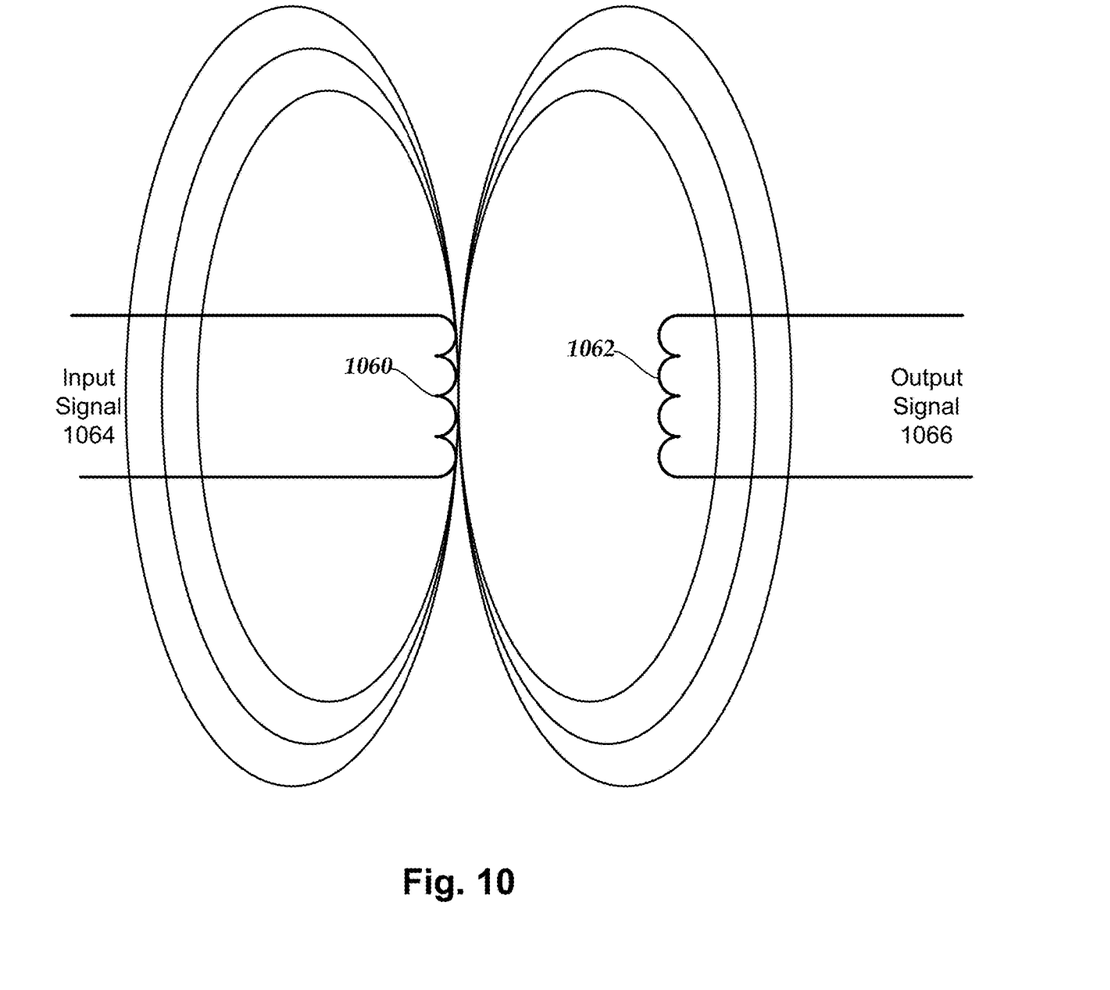
FIG. 10 is a schematic diagram of one embodiment of NFMI communication, according to the invention.

FIG. 10 schematically illustrates NFMI transmission of an input signal 1064 by magnetic field induction from a transmitting coil 1060 (for example, in a NFMI transceiver 802) to a receiving coil 1062 (for example, in a system device 804) to produce an output signal 1066. As an alternative to the transmitting coil 1060 or receiving coil 1062 and other suitable transducer can be used that facilitates NFMI transmission/reception. The use of the term "coil" herein includes other suitable transducers unless indicated otherwise.

NFMI can use any type of analog or digital modulation for signal transmission including, but not limited to, any type of amplitude, frequency, phase, or other modulation. In at least some embodiments, the same coils 1060, 1062 can be used for transferring power to a device by magnetic induction. In other embodiments, different coils or antennas may be used for transferring power to the device. In at least some embodiments, the transmitting coil 1060 and receiving coil 1062, and associated circuitry, can both transmit and receive so that the NFMI transceiver device 802 and system devices 804 can communicate in both directions using NFMI.

Returning to FIG. 8, in at least some embodiments, the NFMI transceiver device 802 can communicate with one or more user devices 806 or the sensor arrangement 320 using any suitable communications arrangement or protocol including, but not limited to, NFMI, Bluetooth™, near field communications (NFC), wireless fidelity (WiFi), satellite communication, cellular communication, Infrared Data Association standard (IrDA), or the like or any combination thereof. In some embodiments, the NFMI transceiver device 802 communicates with at least one user device 806 directly. In some embodiments, the NFMI transceiver device 802 communicates with at least one user device 806 through a network such as, for example, a personal area network (PAN), local area network (LAN), metropolitan area network (MAN), wide area network (WAN), cellular network, the Internet, or any combination thereof. In some embodiments, the NFMI transceiver device 802 communicates to a user device 806 through another user device 806. For example, the NFMI transceiver device 802 may communicate (using, for example, Bluetooth™ or NFC) with a patient's mobile phone (acting as a user device 806) and the patient's mobile phone may communicate (using, for example, cellular communications or WiFi over the Internet or other network or combination of networks) with a server or computer (acting as another user device 806) at a healthcare facility (such as a hospital, clinic, or doctor's office).

Figure 11:
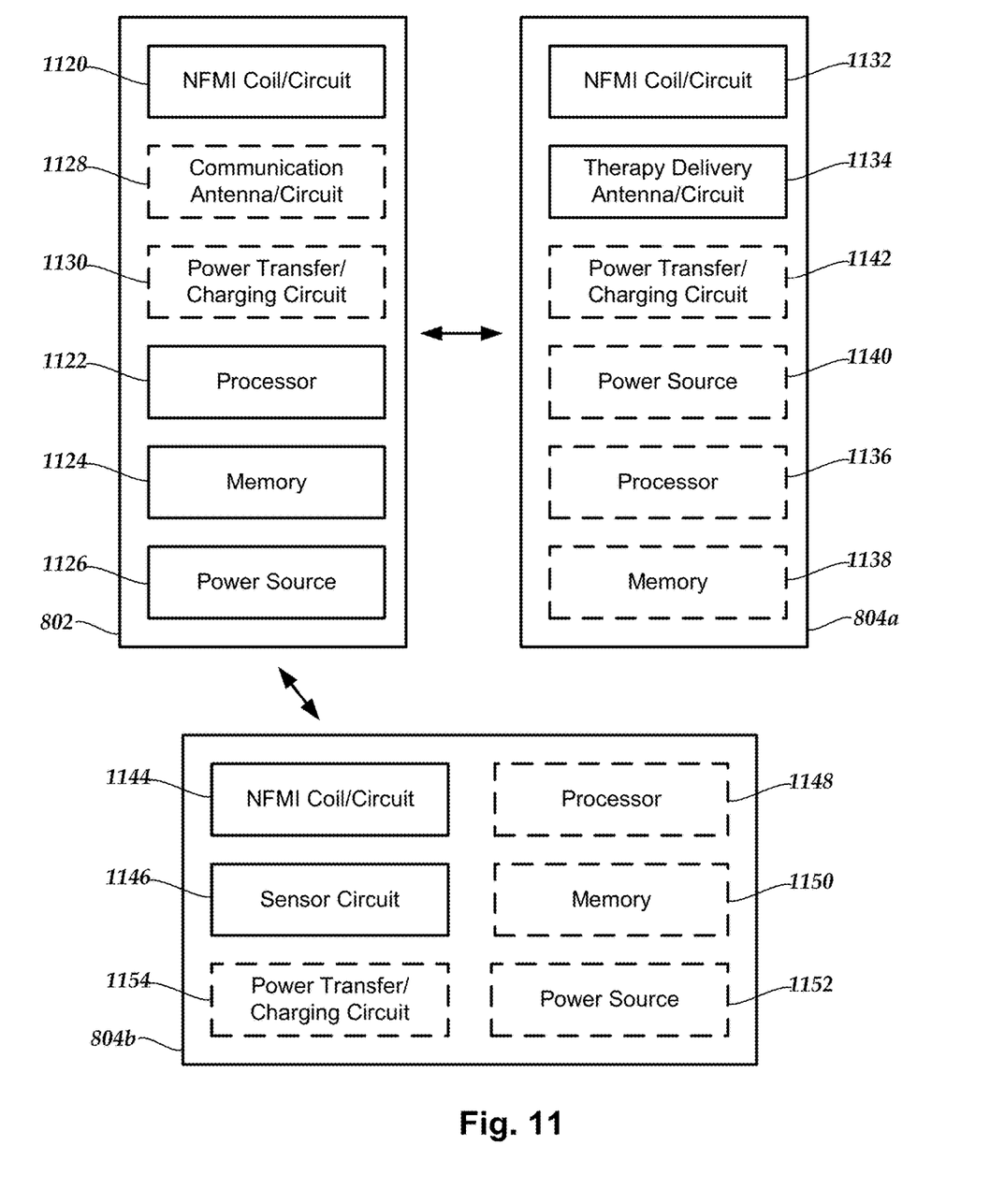
FIG. 11 is a block diagram of one embodiment of system components including a NFMI transceiver device, a therapy delivery device, and a sensor device, according to the invention.

FIG. 11 is a functional block diagram of one embodiment of a NFMI transceiver device 802, one embodiment of a therapy delivery device 804a, and one embodiment of a sensor device 804b. Other embodiments of these devices may include more or fewer components than those illustrated in FIG. 11.

The NFMI transceiver device 802 includes a NFMI coil/transceiver circuit 1120 (i.e., a NFMI transceiver), a processor 1122, a memory 1124, a power source 1126 (for example, a battery), an optional communications antenna/circuit 1128 for communication with a user device 806 (FIG. 8), and an optional power transfer/charging circuit 1130 for transferring power to a therapy delivery device 804a or sensor device 804b. In some embodiments, the optional communications antenna/circuit 1128 provides for communication to a user device 806 (FIG. 8) and can be selected from any suitable communications technique including, but not limited to, Bluetooth™, near field communications (NFC), wireless fidelity (WiFi), satellite communication, cellular communication, Infrared Data Association standard (IrDA), or the like or any combination thereof. In some embodiments, the NFMI transceiver device 802 may communicate with a user device 806 using NFMI.

The therapy delivery device 804a includes a NFMI coil/transceiver circuit 1132 (i.e., a NFMI transceiver) or, alternatively, a NFMI coil/receiver circuit (i.e., a NFMI receiver), a therapy delivery circuit 1134, an optional processor 1136, an optional memory 1138, an optional power source 1140 (for example, a battery), and an optional power transfer/charging circuit 1142 for receiving power from the NFMI transceiver device 802 or other power source. The NFMI coil/transceiver circuit 1132 (or NFMI coil/receiver circuit) receives signals from the NFMI transceiver device.

The sensor device 804b includes a NFMI coil/transceiver circuit 1144 (i.e., a NFMI transceiver) or, alternatively, a NFMI coil/transmitter circuit (i.e., a NFMI transmitter), a sensor circuit 1146, an optional processor 1148, an optional memory 1150, an optional power source 1152 (for example, a battery), and an optional power transfer/charging circuit 1154 for receiving power from the NFMI transceiver device 802 or other power source. The sensor circuit 1146 of the sensor device 804b will depend on the type of sensor that is used. Examples of types of sensors are listed above. The sensor circuit 1146 produces sensor signals based on observation of the patient. These sensor signals may be raw output of the sensor or may be processed (for example, using the processor 1148 or other processing circuitry) to produce modified output of the sensor or even data based on the raw output of the sensor. The NFMI coil/transceiver circuit 1144 (or NFMI coil/transmitter circuit) transmits the sensor signals to the NFMI transceiver device.

The NFMI coil/transceiver circuit 1120, 1132, 1144 include a coil 1060 (FIG. 10) and associated circuitry for transmitting or receiving (or both transmitting and receiving) a signal using magnetic induction to/from a NFMI transceiver device, a therapy delivery device 804a, a sensor device 804b, or a user device 806 (FIG. 8). Any suitable coil and transceiver (or transmitter or receiver) circuit can be used. Examples of coils and transceiver circuits for NFMI transmitting and receiving are known. Examples of NFMI devices include, but are not limited to, those described in U.S. Pat. Nos. 8,838,022; 8,929,809; 9,300,367; 9,455,771; 9,742,471; and 10,015,623, all of which are incorporated herein by reference in their entireties.

The power source 1126, 1140, 1152 can be any suitable power source including, but not limited to, batteries, power cells, or the like or any combination thereof. In at least some embodiments, the power source is rechargeable. In at least some embodiments, the NFMI transceiver device 802 includes a power transfer/charging circuit 1130 that can be used to charge a power source 1140, 1152 in the therapy delivery device 804a or sensor device 804b. In at least some embodiments, the power transfer/charging circuit 1130 may utilize coil of the NFMI coil/transceiver circuit 1120 to deliver power to the therapy delivery device 804a or sensor device 804b. In at least some embodiments, the NFMI coil/transceiver circuit 1132, 1144 of the therapy delivery device 804a or sensor device 804b can receive the power and deliver to the power transfer/charging circuit 1142, 1154. In other embodiments, a separate antenna or coil in the power transfer/charging circuit 1130 may be used to deliver the power to the power transfer/charging circuit 1142, 1154 of the therapy delivery device 804a or sensor device 804b for charging the power source 1140, 1152. In at least some embodiments, a separate charger (not shown) may be used to the charge the power source 1140, 1152 in the therapy delivery device 804a or sensor device 804b. In at least some embodiments, the power source 1126 of the NFMI transceiver 802 may be charged wirelessly or through a wired connection (for example, by attaching a charging cord to a charging port of the NFMI transceiver).

In other embodiments, a therapy delivery device 804a or sensor device 804b may not have a dedicated power source and the NFMI transceiver device 802 (or other device) may deliver power for operation of the therapy delivery device or sensor through the power transfer/charging circuits 1130, 1142, 1154 which may utilize the NFMI coil/transceiver circuits 1120, 1132, 1144.

Any suitable processor 1122, 1136, 1148 can be used including, but not limited to, microprocessors, application specific integrated circuits (ASICs), other integrated circuits, or the like or any combination thereof. Any suitable memory 1124, 1138, 1150 can be used including, but not limited to, RAM, ROM, EEPROM, flash memory, or the like or any combination thereof.

The processor 1136 can be optional in the therapy delivery device 804a. For example, a processor 1136 may be optional if the NFMI signal received by the therapy delivery device 804a produces the desired therapy signal in the therapy delivery circuit 1134. In other embodiments, the processor 1136 in the therapy delivery device 804a can be programmed or otherwise operated using the NFMI signal from the NFMI transceiver device 802 to deliver, or modify delivery of, therapy using the therapy delivery circuit 1134. For example, the NFMI signal from the NFMI transceiver device 802 may include new or updated parameters for therapy delivery, initiate therapy delivery, halt therapy delivery, or the like or any combination thereof. Examples of parameters for therapy delivery include, but are not limited to, amplitude, frequency, or, if pulsed, pulsewidth, pulse duration, or pulse parameter.

The processor 1148 may be optional in the sensor device 804b. For example, a processor 1148 may be optional if the signal from the sensor circuit 1146 can be transmitted to the NFMI transceiver 802 for processing. In other embodiments, the processor 1148 in the sensor device 804b can be programmed or otherwise operated using the NFMI signal from the NFMI transceiver device 802 to operate, or modify operation of, the sensor 804b. The processor 1148 may also process, partially or fully, signals from the sensor circuit 1146 to produce data or signals that are transmitted to the NFMI transceiver device 802. Other processors in the NFMI transceiver device 802 or the user device 806 (or other devices) may fully or partially process data or signals transmitted form the sensor device 804b.

The therapy delivery device 804a includes a therapy delivery circuit 1134. Any suitable therapy delivery circuit 1134 can be used. In at least some embodiments, at least one of the therapy delivery devices 804a has a therapy delivery circuit that generates ultra-low radio frequency energy. In at least some embodiments, the delivery of ultra-low radio frequency energy can be a therapeutic delivery. In at least some embodiments, the therapeutic delivery can be for the treatment of cancer or other diseases or disorder.

Figure 12A:
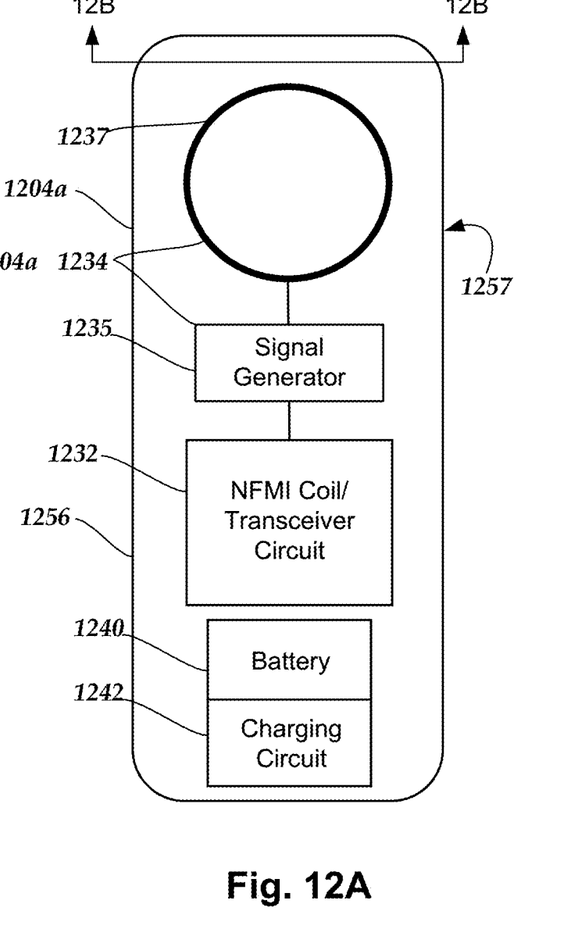
FIG. 12A is a schematic diagram of one embodiment of a therapy delivery device using NFMI communication, according to the invention.
Figure 12B:
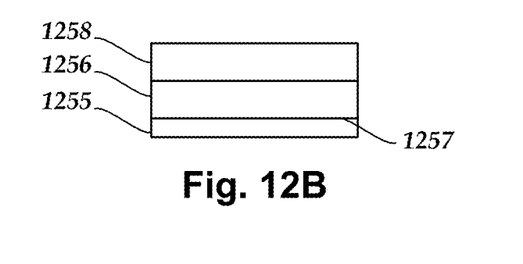
FIG. 12B is a schematic cross-sectional view of a portion of the therapy delivery device of FIG. 12A, according to the invention.

The therapy delivery circuit 1134 can include, for example, a signal generator 1235 (FIG. 12) to produce a therapeutic magnetic signal, such as a therapeutic signal for ultra-low radio frequency energy. The therapy delivery circuit 1134 can also include a transducer 1237 (FIG. 12), for example, a coil or antenna, to deliver the therapeutic magnetic signal to the patient.

FIGS. 12A and 12B illustrate one embodiment of a therapy delivery device 1204a that includes a NFMI coil/transceiver circuit 1232, a therapy delivery circuit 1234 for delivery of a magnetic therapeutic signal such as an ultra-low radio frequency energy signal, a battery 1240 (as a power source), and an optional charging circuit 1242. These elements of the therapy delivery device 1204a are disposed on a substrate 1256 which can be, for example, a flex circuit substrate or any other suitable flexible substrate. In some embodiments, the substrate 1256 can include an adhesive 1255 disposed on a back surface 1257 of the substrate to adhere the therapy delivery device 1204*a* to the skin of the patient, similar to an adhesive bandage. In at least some embodiments, the therapy delivery device 1204*a* may be otherwise attached to the skin of the patient (e.g., using tape or a bandage) or worn by the patient at or near the treatment site. Optionally, a top substrate 1258 can be disposed over the substrate 1256 and the components listed above to provide protection to those components.

Figure 13:
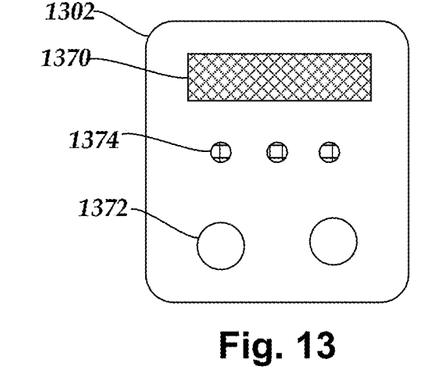
FIG. 13 is a schematic front view of one embodiment of a NFMI transceiver device, according to the invention.

FIG. 13 illustrates one embodiment of a NFMI transceiver device 1302 with some optional features such as a display 1370, one or more buttons 1372 or other input devices (such as a keyboard), and one or more lights 1374. In at least some embodiments, the display 1370 may display instructions or information about operation or warnings or the like or any combination thereof. In at least some embodiments, the lights 1374 may indicate that the NFMI transceiver device is on/off 802, the status of system devices 804, the status of a power source, warnings about low power source or loss of signal or the like or any combination thereof.

In at least some embodiments, the one or more buttons 1372 or other input devices may be used by the patient or other user to direct delivery of therapy or alter therapy parameters or the like or any combination thereof. In at least some embodiments, the delivery of therapy or the alteration of therapy parameters may be restricted to a user with credentials, such as a password or other identification.

In at least some embodiments, the use of NFMI for communication between the NFMI transceiver device and the system devices can enable wireless (e.g., cable free) wearable therapy delivery devices for ultra-low radio frequency energy. In at least some embodiments, the use of NFMI for communication between the NFMI transceiver device and the system devices can enable real-time communication with wearable and implantable therapy delivery devices for ultra-low radio frequency energy. In at least some embodiments, the use of NFMI for communication between the NFMI transceiver device and the system devices can enable relatively low attenuation of communication (into the body of the patient) with implantable therapy delivery devices for ultra-low radio frequency energy.

In at least some embodiments, the use of NFMI for communication between the NFMI transceiver device and the system devices can enable simultaneous operation of a therapy delivery device for ultra-low radio frequency energy and at least one sensor device. In at least some embodiments, the use of NFMI for communication between the NFMI transceiver device and the system devices can enable wireless power transfer to a wearable or implantable therapy delivery device for ultra-low radio frequency energy. In at least some embodiments, the use of NFMI for communication between the NFMI transceiver device and the system devices can enable security of signals between the NFMI transceiver device and the system devices.

In at least some embodiments, the present systems can enable simultaneous communication with a user device or sensor arrangement using Bluetooth™ or other communication techniques. Such communication may allow a user to control the NFMI transceiver device and one or more therapy delivery devices for ultra-low radio frequency energy (and, optionally, one or more sensor devices.)

The above specification provides a description of the invention and the manufacture and use of the invention. Since many embodiments of the invention can be made without departing from the spirit and scope of the invention, the invention also resides in the claims hereinafter appended.

What is claimed as new and desired to be protected is:

1. A measurement system, comprising:
a container configured to contain solvated target molecules; and
a plurality of magnetoresistive (MR) sensor devices, each of the MR sensor devices comprising at least one MR sensor disposed near the container and configured to measure a magnetic field generated by the solvated target molecules, each of the at least one MR sensor comprising a pin layer having a pinned direction of magnetization, a free layer having a direction of magnetization that varies with an applied magnetic field, and a non-conductive layer separating the pin layer and the free layer, wherein the MR sensor devices are arranged along at least three orthogonal directions with respect to the container, wherein the measurement system is configured to make measurements of a magnetic field generated by the solvated target molecules along the at least three orthogonal directions.

2. The measurement system of claim 1, wherein each of the MR sensor devices comprises a plurality of the MR sensors.

3. The measurement system of claim 2, wherein the plurality of MR sensors are arranged in a Wheatstone bridge.

4. A method, comprising: solvating target molecules and placing the solvated target molecules in a container; providing the container with the solvated target molecules in a measurement system comprising a plurality of magnetoresistive (MR) sensor devices, each of the MR sensor devices comprising at least one MR sensor disposed near the container and configured to measure a magnetic field generated by the solvated target molecules, each of the at least one MR sensor comprising a pin layer having a pinned direction of magnetization, a free layer having a direction of magnetization that varies with an applied magnetic field, and a non-conductive layer separating the pin layer and the free layer, wherein the MR sensor devices are arranged along at least three orthogonal directions with respect to the container; using the at least one MR sensor of at least three of the MR sensor devices to acquire a magnetic field generated by the solvated target molecules; and producing signals by the at least one MR sensor of each of the at least three MR sensor devices in response to the acquired magnetic field.

5. The method of claim 4, further comprising amplifying the signals from the at least one MR sensor of at least one of the MR sensor devices and converting the amplified signals into digital signals.

6. The method of claim 5, further comprising delivering the digital signals to a delivery device to simulate the presence of the solvated target molecules.

7. The method of claim 5, further comprising storing the digital signals as a data file in an audio file format.

8. The method of claim 4, wherein each of the MR sensor devices comprises a plurality of the MR sensors.

9. The method of claim 8, wherein the plurality of MR sensors are arranged in a Wheatstone bridge.

10. A therapy delivery system, comprising:
the measurement system of claim 1; and
a near field magnetic induction (NFMI) transceiver device configured to be worn or otherwise disposed on a patient and configured to utilize the measured magnetic field of the measurement system to produce signals for delivery of therapy, the NFMI transceiver device comprising a NFMI transceiver; and
a therapy delivery device comprising
a NFMI receiver configured to receive the signals from the NFMI transceiver device, and a therapy delivery circuit configured to deliver a therapeutic magnetic signal, based, at least in part, on the received signals from the NFMI transceiver device, to the patient when the patient wears the therapy delivery device or has the therapy delivery device disposed on skin of the patient or has the therapy delivery device implanted.

11. The therapy delivery system of claim 10, wherein the NFMI transceiver device further comprises a communications circuit for communication, other than NFMI, to a user device.

12. The therapy delivery system of claim 11, wherein the therapy delivery system further comprises the user device configured to communicate with the NFMI transceiver device through the communications circuit of the NFMI transceiver device.

13. The method of claim 4, further comprising applying a stimulus to the solvated target molecules, wherein using the at least one MR sensor comprises using the at least one MR sensor of the at least three of the MR sensor devices to acquire a magnetic field generated by the solvated target molecules in response to the stimulus.

14. The method of claim 13, wherein the stimulus comprises white noise.

15. The method of claim 4, wherein using the at least one MR sensor comprises applying a DC offset field while using the at least one MR sensor of the at least three of the MR sensor devices to acquire a magnetic field.

16. The measurement system of claim 1, further comprising a DC offset field generator configured for generating a DC offset field for the container.

17. The measurement system of claim 1, further comprising a shield to contain the container and the plurality of MR sensor devices within the shield and configured to reduce or remove an ambient magnetic field within the shield.

18. The measurement system of claim 1, wherein the plurality of MR sensor devices comprises at least four of the MR sensor devices.

19. The measurement system of claim 18, wherein at least three of the MR sensor devices are arranged in a plane around the container.

20. The method of claim 4, further comprising placing the container and the MR sensor devices within a shield configured to reduce or remove an ambient magnetic field within the shield.

* * * * *